(12) United States Patent
Plohnke et al.

(10) Patent No.: US 8,963,103 B2
(45) Date of Patent: Feb. 24, 2015

(54) PROBE FOR LASER MICROSCOPE

(71) Applicant: Carl Zeiss Microscopy GmbH, Jena (DE)

(72) Inventors: Tim Plohnke, Goettingen (DE); Alexander Scheps, Adelebsen (DE); Timo Rojahn, Uslar (DE); Tobias Klinge, Goettingen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/266,373

(22) Filed: Apr. 30, 2014

(65) Prior Publication Data

US 2014/0319380 A1 Oct. 30, 2014

(30) Foreign Application Priority Data

Apr. 30, 2013 (DE) .......................... 10 2013 007 463

(51) Int. Cl.
| | | |
|---|---|---|
| *A61L 2/10* | (2006.01) | |
| *G01N 33/00* | (2006.01) | |
| *G01N 1/28* | (2006.01) | |
| *C12M 1/32* | (2006.01) | |
| *C12M 1/36* | (2006.01) | |

(52) U.S. Cl.
CPC ............... *A61L 2/10* (2013.01); *A61L 2202/16* (2013.01); *A61L 2202/23* (2013.01); *G01N 33/00* (2013.01); *G01N 1/28* (2013.01); *C12M 23/12* (2013.01); *C12M 41/48* (2013.01)
USPC ... 250/455.11; 250/306; 250/307; 250/492.1; 250/504 R; 422/1; 422/22; 422/24; 210/748.11; 210/764

(58) Field of Classification Search
CPC ... A61L 2/10; A61L 2202/16; A61L 2202/23; A61L 2/24; A61L 9/20
USPC ............. 250/306, 307, 455.11, 492.1, 504 R; 210/748.11, 764; 422/1, 22, 24, 28
See application file for complete search history.

(56) References Cited

U.S. PATENT DOCUMENTS

| | | | | |
|---|---|---|---|---|
| 6,008,010 | A * | 12/1999 | Greenberger et al. | .......... 435/41 |
| 7,319,230 | B2 * | 1/2008 | Skaggs | .................... 250/455.11 |
| 8,400,059 | B2 * | 3/2013 | Voronov et al. | ............... 313/610 |
| 2001/0033321 | A1 * | 10/2001 | Sasaki et al. | .................. 347/212 |
| 2005/0035711 | A1 * | 2/2005 | Spielman et al. | ............. 313/567 |

(Continued)

FOREIGN PATENT DOCUMENTS

| | | |
|---|---|---|
| BR | 9000203 | 11/1990 |
| CN | 202570197 | 12/2012 |

(Continued)

OTHER PUBLICATIONS

German Search for German Application No. 10 2013 007 463.0, dated Apr. 8, 2014. English Translation provided.

(Continued)

*Primary Examiner* — Michael Logie
(74) *Attorney, Agent, or Firm* — Patterson Thuente Pedersen, P.A.

(57) ABSTRACT

A device for sterilizing a sample chamber in an automated live cell microscope, having a sample holding frame contained in a housing of the microscope. The device includes a UVC sterilizing unit that emits an ultraviolet light with a wavelength of 280 nm to 100 nm (UVC radiation). The UVC sterilizing unit is arranged so that it is able to travel through the sample chamber for sterilization purposes.

12 Claims, 5 Drawing Sheets

(56) References Cited

U.S. PATENT DOCUMENTS

| | | |
|---|---|---|
| 2005/0051723 A1* | 3/2005 | Neagle et al. .................. 250/306 |
| 2005/0061743 A1* | 3/2005 | Buttner ........................ 210/646 |
| 2006/0011856 A1* | 1/2006 | Skaggs .................... 250/455.11 |
| 2006/0263275 A1* | 11/2006 | Lobach ........................ 422/186 |
| 2007/0121200 A1 | 5/2007 | Suzuki et al. |
| 2007/0284541 A1* | 12/2007 | Vane ........................ 250/441.11 |
| 2011/0305597 A1* | 12/2011 | Farren ............................ 422/24 |
| 2013/0175460 A1* | 7/2013 | Farren ........................ 250/504 R |
| 2014/0161663 A1* | 6/2014 | Farren et al. .................... 422/24 |

FOREIGN PATENT DOCUMENTS

| | | |
|---|---|---|
| DE | 102010033446 A1 | 2/2012 |
| EP | 2416346 | 2/2012 |
| EP | 2799092 | 4/2014 |
| WO | WO 98/20108 | 5/1998 |

OTHER PUBLICATIONS

Brochure: MagNA STARLet, Hamilton Robotics Ltd., Copyright 2006; 7 pgs.

EP Search Report, German Version for German Application No. DE14165999.5, dated Sep. 18, 2014. No English translation provided.

WPI/Thompson, vol. 1990, No. 50, re H.R. Mazurkevicius, NPL Reference No. XP002729198, corresponds to EP2799092, cited herein.

\* cited by examiner

PROBE FOR LASER MICROSCOPE

RELATED APPLICATION

The present application claims priority to German Application No. 10 2013 007 463.0 filed Apr. 30, 2014, said priority application being incorporated herein in its entirety by reference.

FIELD OF THE INVENTION

The invention relates to a device for sterilizing a sample chamber in a microscope. More specifically, the invention relates to sterilization of a sample chamber in an automated live cell microscope by using an ultraviolet light sterilizing unit.

BACKGROUND OF THE INVENTION

In order to achieve best results in live cell microscopy, it is important to ensure that the samples are handled and observed in a sterile environment. In conventional research microscopes, it is common practice to disinfect components that come into contact with the sample by wiping them with solvents or by autoclaving them. It is also known to expose the entire microscope to UVC radiation, in other words an ultraviolet radiation with a wavelength of 280 nm to 100 nm.

In automated microscopy, these methods function to only a limited degree due to structural differences from conventional microscopes. Automated microscopes are frequently embodied as closed systems and are known by the term "box microscope." In this case, it is labor-intensive and time-consuming to access the internal spaces in order to sterilize them. These previously known methods cannot be automated.

It is known in the prior art to sterilize a sample chamber with UVC-emitting low-pressure gas discharge tubes. For example, in a publication known as "MagNa STARLet," a product brochure from Hamilton Robotics Ltd, a liquid-handling robot is described that contains permanently installed, UVC-emitting low-pressure gas discharge tubes. According to the publication, this can ensure a continuously sterile environment. A drawback of this device, however, is that it is difficult to implement for space reasons.

The patent specification WO 98/20108 also describes a method for autoclaving a sample chamber. A disadvantage of that device, however, is that the sample chamber must be disassembled in order to access the components to be sterilized. This is a time-consuming process that is not a reasonable option for automated live cell microscopy.

SUMMARY OF THE INVENTION

Based on the disadvantages of the aforementioned prior art solutions, an object of embodiments of the invention is a device for sterilizing a sample chamber in a live cell microscope implemented in such a way that stable environmental conditions are insured in a space to be incubated that is as small as possible. This object can be attained with a devices and methods as herein disclosed.

According to embodiments of the invention, a UVC sterilizing unit in a live cell microscope is arranged so that it is able to travel through the sample chamber for sterilization purposes. A UVC sterilizing unit can also be accommodated in stationary fashion in a kind of parked position in the automated live cell microscope so that it can be introduced into the sample chamber for sterilization purposes. Likewise, a UVC sterilizing unit could also be inserted into an existing sample holding frame.

In an advantageous embodiment, the sterilizing unit is embodied in the form of a swappable element, with the housing of the live cell microscope being provided with a swapping region for selectively accommodating the sample holding frame or the UVC sterilizing unit. To this end, the sample holding frame or the UVC sterilizing unit can be arranged on an XY table located inside the housing of the live cell microscope and can be introduced into the swapping region in an automated fashion. From the swapping region, either the sample holding frame or the UVC sterilizing unit travels through the sample chamber with various traveling methods (traveling modes) and they can then be detached from the XY table again when they are in the swapping region.

The receiving contours for immobilizing the sample holding frame and the sterilizing unit and the dimensions thereof are embodied to enable a quick swapping in the transfer region. In embodiments of the invention, the sample holding frame and the UVC sterilizing unit have the same dimensions and the same movement range so as to ensure that a complete sterilization is carried out.

In another advantageous embodiment, this immobilization of the sample holding frame or UVC sterilizing unit is provided by means of clamped connections to the XY table. The receiving contours have openings in which a cam lever respectively mounted on the XY table can engage from a horizontal clamping position into a vertical release position.

The sterilizing unit is advantageously equipped with low-pressure gas discharge tubes and the required ignition and operating voltage is produced by means of an inverter circuit. The device may also be equipped with other UVC-emitting illumination means such as LEDs, mercury vapor lamps, or quartz halogen lamps. Another embodiment includes placing the UVC-emitting illumination elements in the side walls or floor and ceiling of the travel region (sample chamber). A stationary light beams light into the whole travel region by means of a mirror. The arrangement of mirrors makes it possible to illuminate every corner, preventing shadows from being cast. Since there are regions of the side walls of the travel region that may not be sufficiently illuminated for structural reasons, before the movement of the UVC sterilizing unit in the XY direction in the travel region, movement can occur in the Z direction.

For purposes of supplying the required ignition and operating voltage (24 volts), the UVC sterilizing unit can advantageously provided with contacts that are embodied in the form of spring contacts. Two contacts may be used for detecting the sample holding frame and UVC sterilizing unit and two contacts may be used for supplying voltage to the low-pressure gas discharge tubes.

In another advantageous embodiment aimed at reducing absorption losses due to the supporting mechanics in the region to be sterilized, the housing of the UVC sterilizing unit may have a number of cut-outs. These cut-outs can be kept relatively large and the dividing pieces may be kept relatively small without a loss of stability.

It may also be advantageous if means are provided for changing the speed of the movement of the UVC sterilizing unit in the travel region of the sample chamber. This is advantageous when, for structural reasons, the distance of the UVC sterilizing unit from the wall of the sample chamber is different or when there are regions that are more seriously contaminated. This change can occur in an automated fashion by means of a corresponding programming or can be preset directly by the user.

BRIEF DESCRIPTION OF THE DRAWINGS

The embodiments of the present invention may be more completely understood in consideration of the following detailed description of various embodiments in connection with the accompanying drawings, in which.

Figure 1:
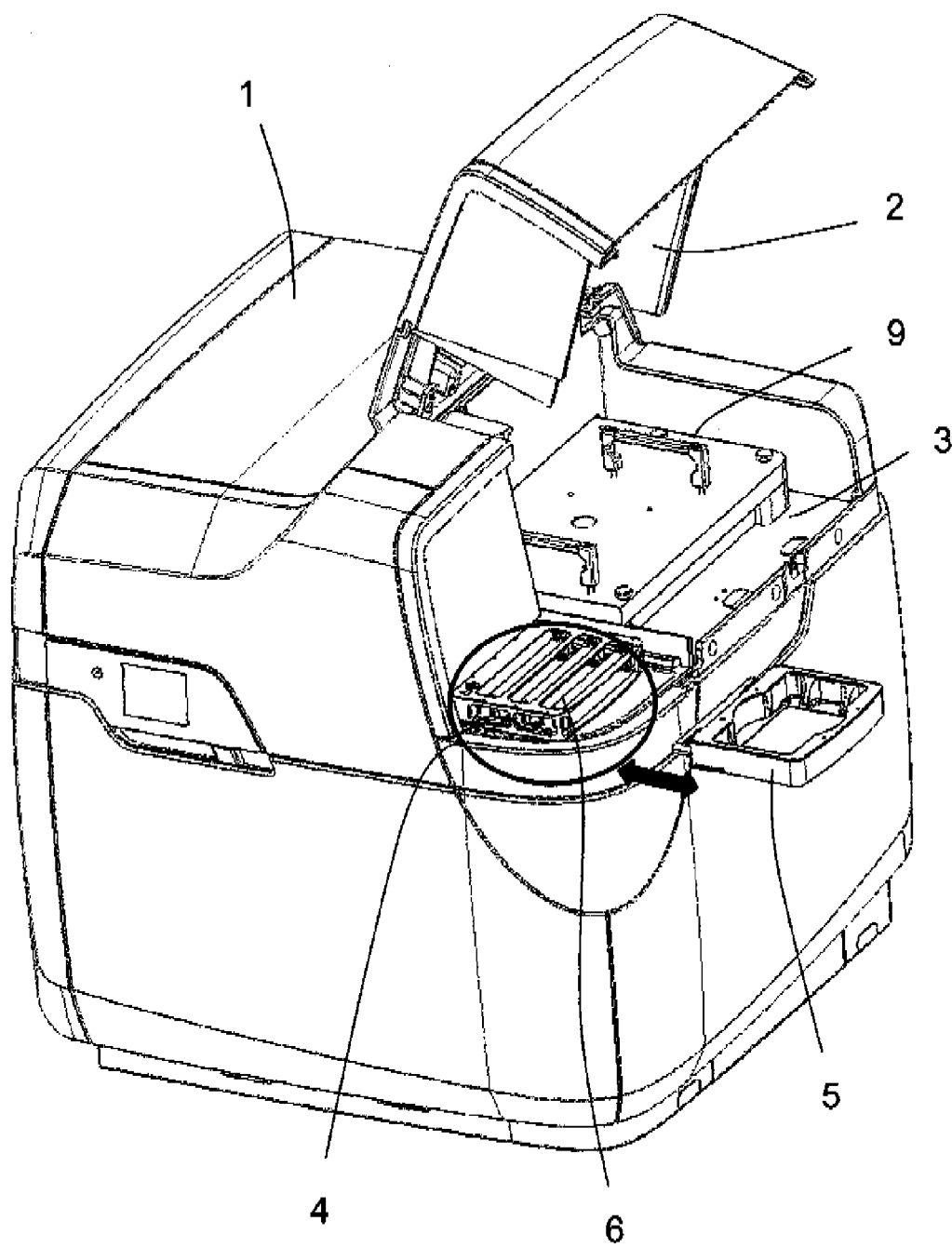
FIG. 1 depicts an automated live cell microscope according to an embodiment of the invention.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION OF THE DRAWINGS

FIG. 1 depicts an automated live cell microscope on whose housing 1 a device door 2 is provided for opening a sample chamber 3. The live cell microscope has a swapping region 4 for selectively accommodating a sample holding frame 5 or a UVC sterilizing unit 6 that emits light with a wavelength of 280 nm to 100 nm. As is depicted in FIG. 1, the UVC sterilizing unit 6 is situated in the swapping region 4. Both the sample holding frame 5 and the UVC sterilizing unit 6 are arranged on an XY table 7 (FIG. 4), and travel one after the other through a transfer region 8 and a defined travel region 9 in the sample chamber 3, as shown in greater detail in FIG. 3, and then continue on into the swapping region 4 in order to be swapped.

Figures 2A, 2B:
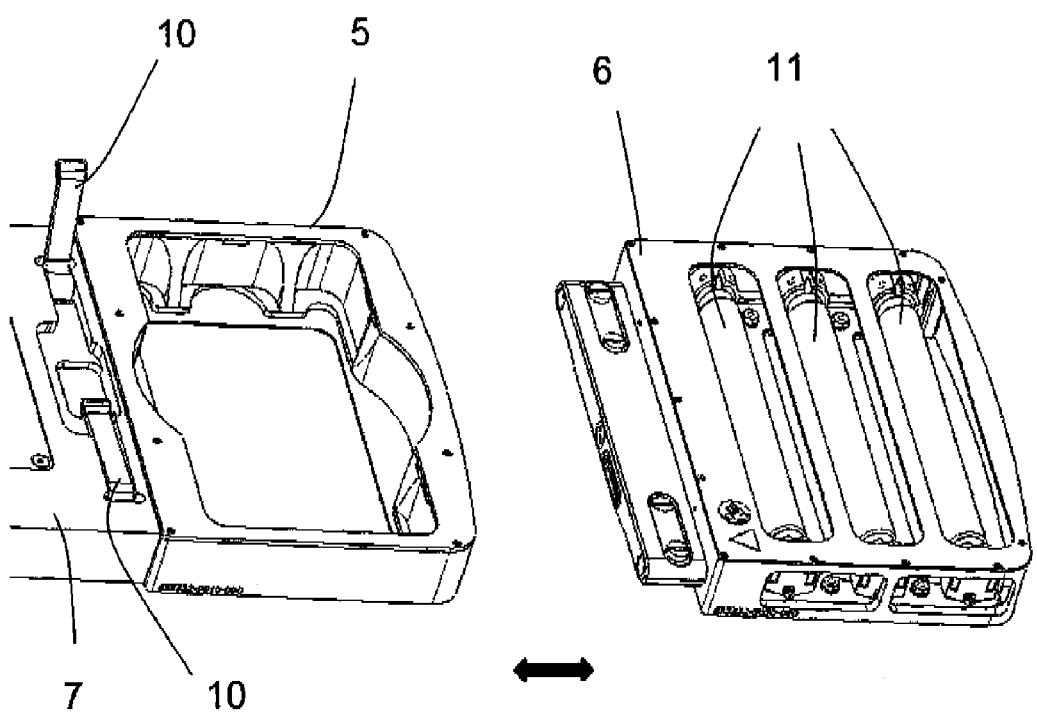
FIG. 2a depicts a sample holding frame of a microscope according to an embodiment of the invention.
FIG. 2b depicts a UVC sterilizing unit according to an embodiment of the invention.

FIG. 2a depicts a sample holding chamber 5, which is affixed to the XY table 7 via a clamped connection. Two cam levers 10 are fastened to the XY table, extend through corresponding openings in the sample holding frame 5, and are brought from a vertical release position into a horizontal clamping position. In the release positions, the sample holding frame 5 and the UVC sterilizing unit 6 can be pulled laterally out of the swapping region 4. The same connection contours as the sample holding frame 5 are provided for the UVC sterilizing unit 6 depicted in FIG. 2b, which is equipped with three low-pressure gas discharge tubes 11.

Figure 3:
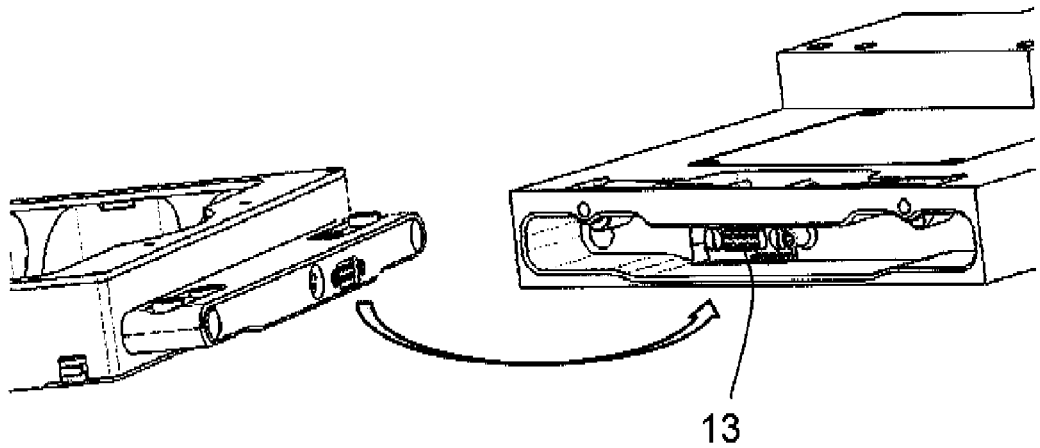
FIG. 3 depicts a power supply for a sterilizing unit according to an embodiment of the invention.

For purposes of automated detection of the sample holding frame 5 and UVC sterilizing unit 6, the sample holding frame 5 and the UVC sterilizing unit 6 are provided with spring contacts (not shown) whose impetuses can be detected by a programmable microcontroller (not shown), which may be for example a known 1-wire EPROM. At the same time, the spring contacts 13 ensure the supply of current (FIG. 3).

Figure 4:
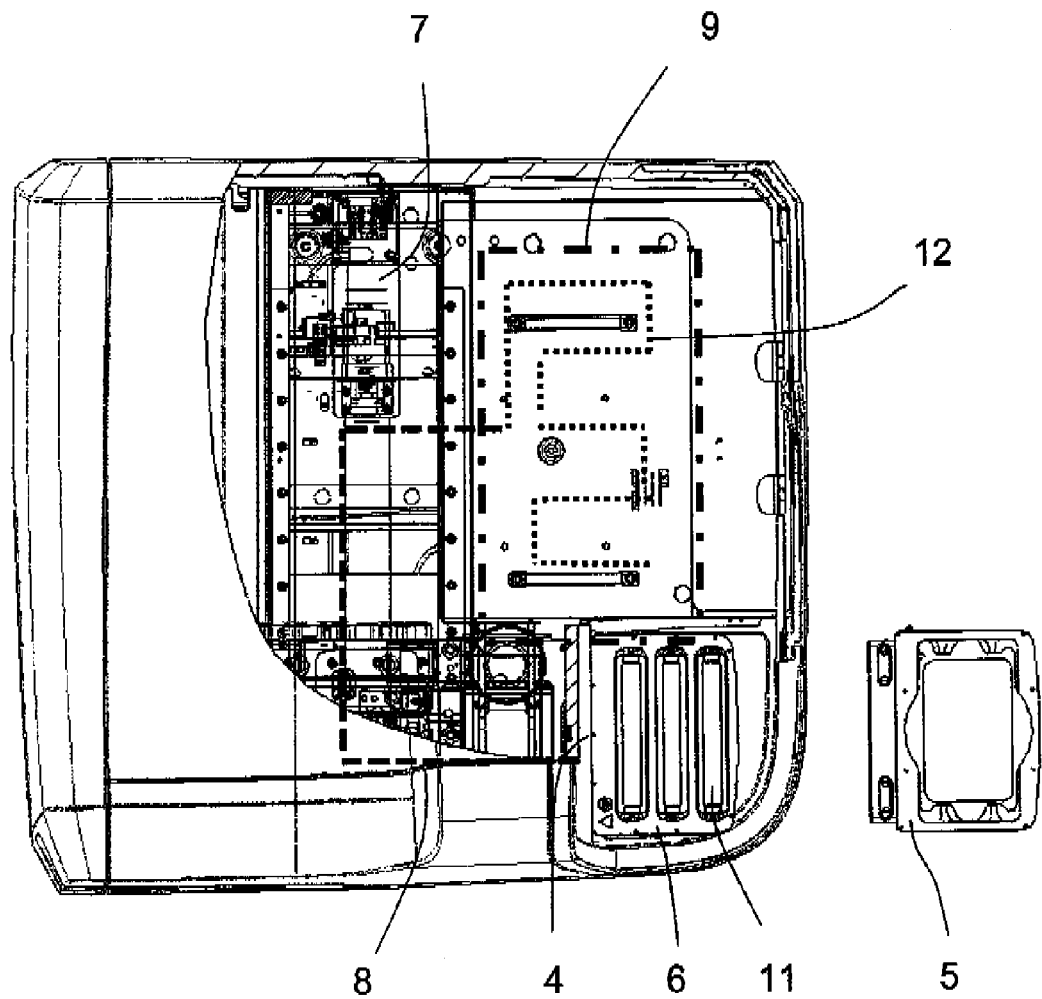
FIG. 4 depicts a transfer and travel region.
Figure 5:
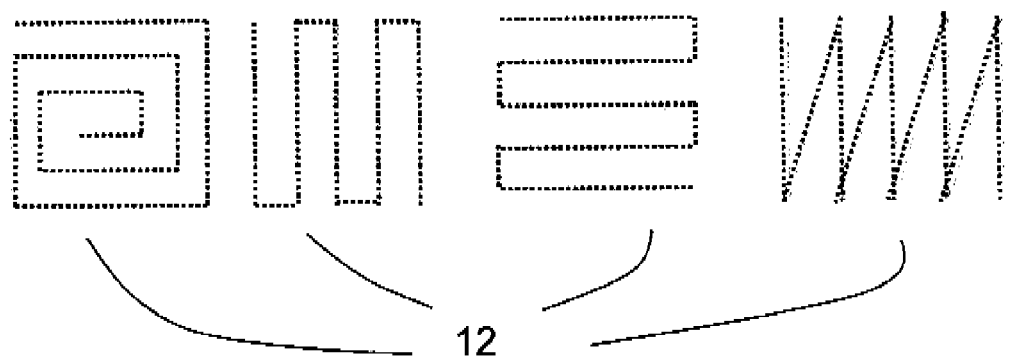
FIG. 5 depicts travel modes.

FIG. 4 depicts a top view of the automated live cell microscope, with the XY table 7 for selectively accommodating the sample holding frame 5 or the UVC sterilizing unit 6, and also depicts the swapping region 4 of the transfer region 8, the travel region 9, the traveling modes 12, and the UVC sterilizing unit 6 mounted on the XY table 7. The sample holding frame 5 here is in the standby position. FIG. 5 depicts the different traveling modes 12 of the sample holding frame 5 or UVC sterilizing unit 6.

After immobilization in the swapping region 4, the XY table 7 in the UVC sterilizing unit 6 travels through the transfer region 8 into the travel region 9. Two spring elements (not shown) provide the voltage supply of 24 volts, which is produced by an inverter circuit that produces the required ignition and operating voltage for the low-pressure gas discharge tubes 11. The voltage for the UVC sterilizing unit 6 is switched on by a control unit, after which a check is performed to make sure that the introduced unit is in fact the UVC sterilizing unit 6. A check is also performed as to whether all of the safety-relevant housing openings for the process are closed.

The completed immobilization of the UVC sterilizing unit 6 in the swapping region 4 is confirmed by an input. The UVC sterilizing unit 6 is moved behind the last shutter cover, which then closes. After the successful closing of the shutter cover, a signal is generated and the UVC sterilizing unit 6 is switched on and emits the UV radiation. Then the UVC sterilizing unit 6 travels into the housing 1 of the live cell microscope and irradiates the entire transfer region 8 and travel region 9 inside the live cell microscope, either by means of a scanning motion or in step-by-step fashion. The sample holding frame 5 can in the meantime be autoclaved in a conventional way.

The UVC sterilizing unit 6 can be produced by coarse free-milling procedures so that the UVC radiation emitted by the low-pressure gas discharge tubes 11 can propagate in the region to be sterilized (sample chamber 3) with as few absorption losses as possible due to the supporting mechanics. This is achieved in that the cut-outs in the UVC sterilizing unit are as large as possible and the dividing pieces are as small as possible without negatively affecting the stability. One embodiment is depicted in FIG. 2b.

The irradiation times can vary in different regions. In order to scan the entire travel region 9, the traveling motion can be executed in a wide variety of modes 12. Possible variants in the XY direction are depicted in FIG. 4.

After the full sterilization has been completed, the UVC sterilizing unit 6 travels back into the swapping region 4. Here, as described above, it is swapped out for the sample holding frame 5. The automated live cell microscope can then be used again.

The foregoing descriptions present numerous specific details that provide a thorough understanding of various embodiments of the invention. It will be apparent to one skilled in the art that various embodiments, having been disclosed herein, may be practiced without some or all of these specific details. In other instances, components as are known to those of ordinary skill in the art have not been described in detail herein in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention. Accordingly, this application is intended to cover any adaptations or variations of the invention.

For purposes of interpreting the claims for the present invention, it is expressly intended that the provisions of 35 U.S.C. §112(f) are not to be invoked unless the specific terms "means for" or "step for" are recited in a claim.

The invention claimed is:

1. A device for sterilizing a sample chamber in an automated live cell microscope, the microscope having a sample holding frame contained in a housing of the microscope and fastening, operating, and control elements for immobilizing and introducing movement in into the sample holding frame, the device comprising a UVC sterilizing unit that emits an ultraviolet light with a wavelength of 280 nm to 100 nm, the unit being arranged to travel through the sample chamber, wherein the UVC sterilizing unit is a swappable element, the housing of the live cell microscope being providing with a swapping region for selectively accommodating the sample holding frame or the UVC sterilizing unit such that the sample holding frame or the UVC sterilizing unit are alternatively arranged on an XY table located inside the housing, the sample holding frame or the UVC sterilizing unit is introduced into the swapping region traveling through the sample chamber and detached from the XY table in the swapping region, and wherein the XY table has structure for alternatively receiving the sample holding frame and the UVC sterilizing unit.

2. The device of claim 1, wherein the UVC sterilizing unit is integrated into the live cell microscope.

3. The device of claim 1, wherein the structure is a clamped connection.

4. The device of claim 1, wherein the sample holding frame and the UVC sterilizing unit each include openings in which a cam lever respectively mounted on the XY table can engage from a horizontal clamping position into a vertical release position.

5. The device of claim 1, wherein for purposes of detecting the sample holding frame and the UVC sterilizing unit, the sample holding frame and the UVC sterilizing unit are provided with contacts detectable by a programmable microcontroller.

6. The device of claim 5, wherein a 1-wire EPROM is used as the microcontroller.

7. The device of claim 1, wherein the UVC sterilizing unit is equipped with low-pressure gas discharge tubes.

8. The device of claim 7, wherein for purposes of supplying the ignition and operating voltage required for the low-pressure gas discharge tubes, the UVC sterilizing unit is provided with contacts.

9. The device of claim 8, wherein the contacts are spring contacts, two spring contacts being used for detecting the sample holding frame and UVC sterilizing unit and two contacts being used for supplying voltage to the gas discharge tubes, and wherein an inverter circuit is provided to produce required ignition and operating voltages to the gas discharge tubes.

10. The device of claim 1, wherein the housing of the UVC sterilizing unit has a plurality of cut-outs and a plurality of dividing pieces, the cut-outs being kept relatively large and the dividing pieces being kept relatively small.

11. The device of claim 1, further comprising means for changing a speed of the movement of the UVC sterilizing unit in the travel region of the sample chamber.

12. The device of claim 11, wherein actuation of the means for changing the speed of the movement of the UVC sterilizing unit can be adjusted in an automated (programmed) fashion or can be preset by the user.

* * * * *